(12) United States Patent  (10) Patent No.: US 8,267,609 B2
Levine  (45) Date of Patent: Sep. 18, 2012

(54) VIAL FOR DELIVERING CONTENTS ONTO A SUBSTRATE

(75) Inventor: Jonathan B. Levine, Purchase, NY (US)

(73) Assignee: JBL Radical Innovations, LLCDE (US)

( * ) Notice: Subject to any disclaimer, the term of this patent is extended or adjusted under 35 U.S.C. 154(b) by 349 days.

(21) Appl. No.: 12/726,675

(22) Filed: Mar. 18, 2010

(65) Prior Publication Data

US 2010/0266981 A1    Oct. 21, 2010

Related U.S. Application Data

(63) Continuation-in-part of application No. 12/407,013, filed on Mar. 19, 2009, and a continuation-in-part of application No. 12/691,766, filed on Jan. 22, 2010.

(51) Int. Cl.
*B43M 11/06* (2006.01)
(52) U.S. Cl. .......................................... 401/183; 433/89
(58) Field of Classification Search .......... 401/132–135, 401/183–186; 433/80, 88, 89; 222/631, 222/212; 132/112, 116
See application file for complete search history.

(56) References Cited

U.S. PATENT DOCUMENTS

| | | |
|---|---|---|
| 3,972,331 A | 8/1976 | Bolduc et al. |
| 4,279,527 A | 7/1981 | Moe et al. |
| 4,748,990 A | 6/1988 | Brown et al. |
| 4,927,283 A | 5/1990 | Fitjer |
| 5,307,953 A | 5/1994 | Regan |
| 5,509,744 A | 4/1996 | Frazier |
| 5,693,313 A | 12/1997 | Shiraishi et al. |
| 5,857,796 A | 1/1999 | Waldmann |
| D413,730 S | 9/1999 | Frazier |
| D416,389 S | 11/1999 | Frazier |
| 6,254,297 B1 | 7/2001 | Frazier |
| 6,623,272 B2 | 9/2003 | Clemans |
| 6,648,904 B2 | 11/2003 | Altshuler et al. |
| 6,726,482 B2 | 4/2004 | Atkins et al. |
| 6,755,586 B1 | 6/2004 | Frazier |
| D495,843 S | 9/2004 | Frazier |
| D504,775 S | 5/2005 | Frazier |
| 6,902,397 B2 | 6/2005 | Farrell et al. |
| 6,929,475 B1 | 8/2005 | Dragan |

(Continued)

OTHER PUBLICATIONS

Carol Lewis, "Fighting Gum Disease: How to Keep Your Teeth" US Food and Drug Admin., FDA Consumer magazine, May-Jun. 2001 pp. 1-9.

(Continued)

*Primary Examiner* — David Walczak
*Assistant Examiner* — Jennifer C Chiang
(74) *Attorney, Agent, or Firm* — H. Jay Spiegel

(57) ABSTRACT

Dispenser that dispenses a substance onto a substrate, such as a tooth treatment compound onto teeth, includes a vial including a cavity containing the substance and a projecting portion extending outward from the base. An applicator tip is engaged with the conduit and includes an internal passage communicating with the cavity, and an applicator portion situated forward of the conduit and that includes a plurality of spaced-apart projections at a distal application surface, preferably crenellated fingers. A cap is removably attachable to the vial and when attached, the applicator portion of the applicator tip is accommodated in a cavity of the cap and a sealing stopper extends into the internal passage to thereby seal it. When the cap is removed from the vial and the base is squeezed, the substance is urged out of the cavity through the passage of the applicator tip and onto the projections.

17 Claims, 6 Drawing Sheets

U.S. PATENT DOCUMENTS

| | | |
|---|---|---|
| 7,004,657 B2 | 2/2006 | Frazier |
| 7,004,756 B2 | 2/2006 | Andersen |
| 7,021,848 B1 * | 4/2006 | Gruenbacher et al. ............ 401/1 |
| 7,070,413 B1 | 7/2006 | Wagner |
| 7,160,111 B2 | 1/2007 | Baughman |
| 7,201,577 B2 | 4/2007 | Levine |
| 7,597,497 B2 | 10/2009 | Levine |
| 7,740,479 B2 * | 6/2010 | Allred et al. .................... 433/90 |
| 2003/0198918 A1 | 10/2003 | Dragan et al. |
| 2007/0020028 A1 | 1/2007 | Levine |
| 2007/0122769 A1 | 5/2007 | Levine |
| 2007/0166666 A1 | 7/2007 | Levine |
| 2007/0183988 A1 | 8/2007 | Prosise et al. |
| 2008/0245380 A1 * | 10/2008 | Ecker et al. ................... 132/114 |
| 2009/0152267 A1 | 6/2009 | May et al. |
| 2009/0277912 A1 * | 11/2009 | Wang ........................... 220/526 |

OTHER PUBLICATIONS

Klever, CJ et al "In vitro tooth whitening by a sodium bicarbonate/peroxide dentifrice" (J. Clin Dent. 1998), pp. 1-2.

* cited by examiner

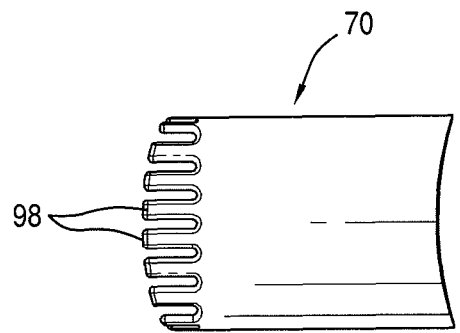
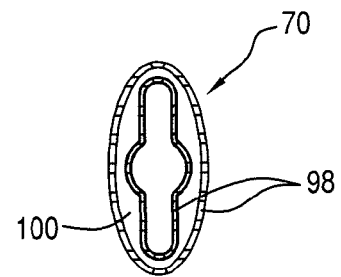
FIG. 16    FIG. 17
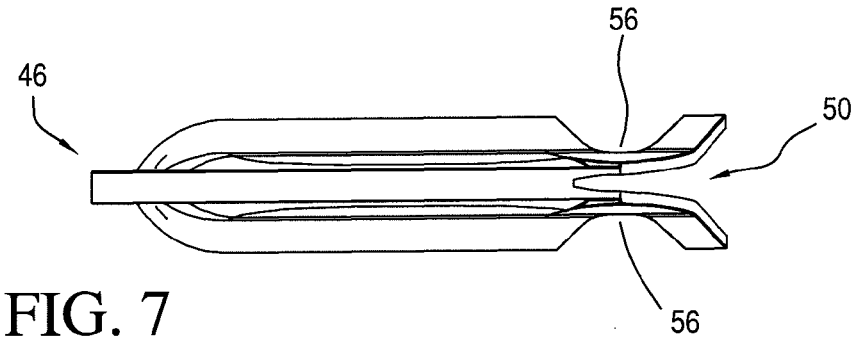
FIG. 7
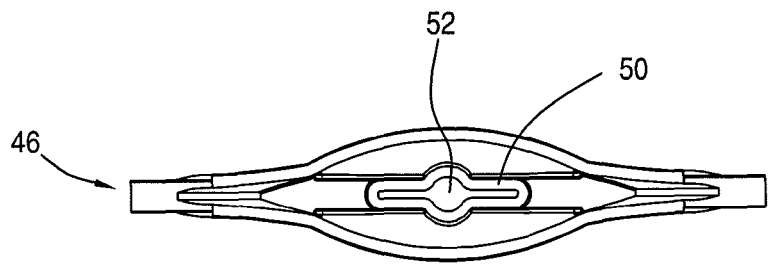
FIG. 8
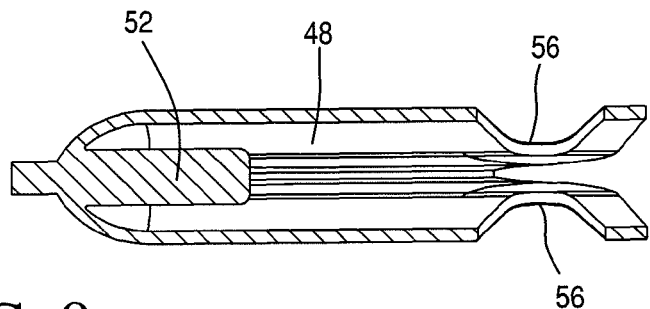
FIG. 9

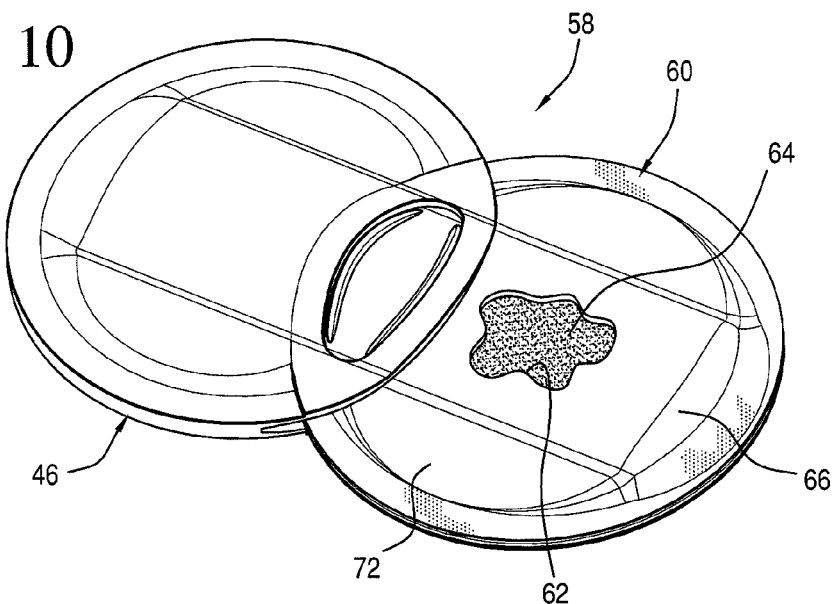
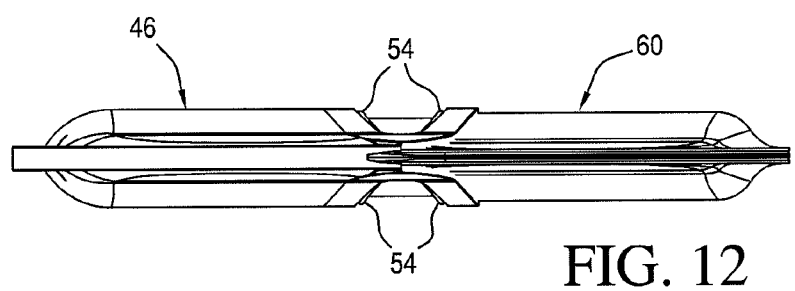
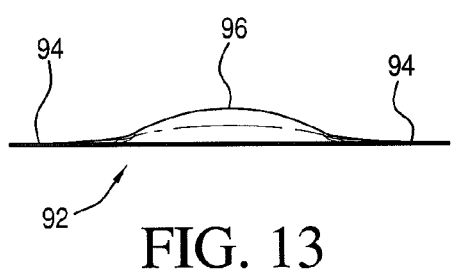
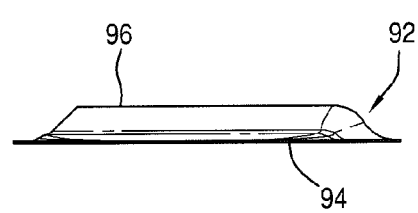
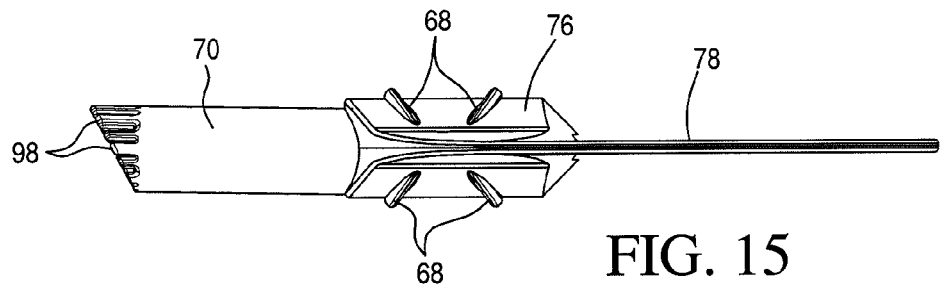

VIAL FOR DELIVERING CONTENTS ONTO A SUBSTRATE

CROSS-REFERENCE TO RELATED APPLICATIONS

This application is a continuation-in-part of U.S. patent application Ser. No. 12/407,013 filed Mar. 19, 2009 and U.S. patent application Ser. No. 12/691,766 filed Jan. 22, 1010, both of which are incorporated by reference herein.

FIELD OF THE INVENTION

The present invention relates generally to a vial suited to deliver a dispensable substance onto a substrate, such as an anatomical part, and methods for applying a substance from such a vial onto a substrate, such as an anatomical part.

The present invention relates more specifically, to a vial suited to deliver substances onto teeth and methods for treating teeth. Dental treatments that can be performed using the vial include, but are not limited to, whitening teeth, desensitizing teeth, and treating teeth to prevent periodontal disease.

BACKGROUND OF THE INVENTION

The delivery of topical medicine from a vial to skin to treat skin conditions or to penetrate the skin for medicinal purposes is known. Likewise, the delivery of tooth whitener gel compositions from a vial is known.

For example, U.S. Pat. No. 7,201,577 discloses a tooth whitener applicator and method. The applicator is a conventional glass ampoule having a tooth whitening solution vacuum-sealed within a chamber of the ampoule. The whitening solution is a liquid based gel containing a whitening formula.

Further, U.S. Pat. No. 7,597,497 discloses a dispenser and applicator for liquid, such as a tooth whitening composition, including a container having an internal chamber and an opening initially sealed by a seal such that liquid within the chamber is hermetically sealed therein, a porous applicator mounted on the container above the opening and overlying the seal, and an over-cap covering the applicator and opening and which is movable with respect to the container and carries a piercing member. The over-cap is movable from a position at which the piercing member is spaced from the seal to a position at which the piercing member extends through the applicator and pierces the seal. The porous applicator includes an opening sized to receive the piercing member. The piercing member is disposed in the opening when the piercing member is spaced from the seal, and the porous applicator is formed of a material having a sufficiently high density that the opening narrows when the piercing member is removed from the opening, to preclude free flow of liquid through the opening.

Additional prior art relating to hand-held dispenser of tooth whitening composition or other dispensable substances include U.S. Published Patent Application No. 2003/0198918, and U.S. Pat. Nos. 3,972,331, 4,927,283 and 5,307,953.

SUMMARY OF THE INVENTION

One aspect of the invention resides in a flexible plastic vial. One end of the vial is preferably closed and the other preferably plugged. The plugged end opens as a plug is pulled out. This allows the contents of the vial to be squeezed out through a channel to reach an applicator and thereby be applied onto a substrate.

There is a mating structure that closes the open end of the flexible vial in a retracted relative position and that opens the open end of the flexible vial in a cleared relative position. The vial is partly flexible to narrow an interior volume under manual squeezing pressure so that when the open end of the vial is open and no longer plugged by the mating structure, contents (such as a gel) within the interior of the vial are urged out of the interior volume to pass though the channel in the applicator tip as the flexible portion of the vial is flexed under the manual squeezing pressure.

The squeezing of the flexible plastic vial narrows the interior accordingly, which tends to urge the contents, such as the tooth whitening composition gel, toward the path of least resistance—toward the open end to pass through the channel in the applicator tip. Further, by pointing the applicator tip downward and thereby the open end of the vial, gravity will assist in urging the contents, such as the tooth whitening composition gel, toward the open end.

The contents of the flexible vial may be a tooth whitening composition gel of any desired viscosity, including those of relatively high viscosities so as to better adhere to teeth surfaces to be whitened than would otherwise be the case for tooth whitening compositions of lesser viscosity. For applications other than dentistry in which the contents are delivered to a surface of a tooth, the contents may be delivered to other areas of the body. That also needs the formulary to be in a hermetically sealed environment. For instance, a pharmaceutical application would deliver a topical medicine or emollient to a skin surface for treatment of a medical malady, such as skin diseases, burns and other applications such as those requiring the pharmaceutical to penetrate through pores in the skin and the formulation needs to be in a hermetically sealed chamber for stability purposes. In other applications, the contents could be an alternative medicine remedy, herbal extract or other medicinal remedy, or be used to color the skin and/or for cosmetic purposes.

The present invention, therefore, addresses the need for applying relatively small portions of gel to an area to be treated, such as a tooth surface, even providing easy access to rear teeth without the need to place fingers in the mouth. Indeed, the present invention fulfills the need to provide an airtight seal of the vial contents and enable reseal the vial contents in a manner that is equally airtight. The present invention also enables even spreading of the gel onto an area to be treated, such as a tooth surface. The present invention also dispenses the product contents of the vial in a manner such that little unused product contents remain after exhausting the manual squeezing of the flexible portion of the vial. The present invention may be easily manufactured and filled at relatively high production rates.

BRIEF DESCRIPTION OF THE DRAWINGS

For a better understanding of the present invention, reference is made to the following description and accompanying drawings, while the scope of the invention is set forth in the appended claims:

FIG. 7 is a front view of a cap of the dispenser shown in FIG. 1;

FIG. 8 is a side view of the cap of the dispenser shown in FIG. 1;

FIG. 9 is a cross-section of the cap of FIG. 7 taken along the line 9-9 in FIG. 2;

FIG. 10 is an isometric view of a second embodiment of a dispenser in accordance with the invention, partly broken away to show an interior;

FIG. 12 is a side view of the dispenser shown in FIG. 10;

FIG. 13 is a front view of a thin member of the vial of the dispenser shown in FIG. 10;

FIG. 14 is a front view of a thin member of the vial of the dispenser shown in FIG. 10;

FIG. 15 is a side view of part of the dispenser shown in FIG. 10;

FIG. 16 is a top view of an applicator tip of the dispenser shown in FIG. 10; and FIG. 17 is a front view of an applicator tip of the dispenser shown in FIG. 10.

DETAILED DESCRIPTION OF PREFERRED EMBODIMENTS

Figure 1:
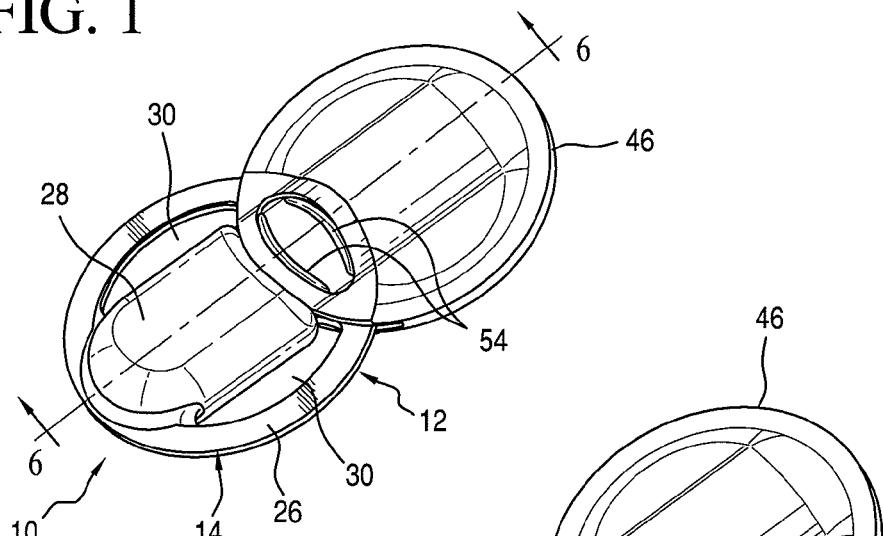
FIG. 1 is a perspective view of a first embodiment of a dispenser in accordance with the invention.

Referring now to the accompanying drawings wherein the same reference numerals refer to the same or similar elements, FIG. 1 shows a perspective view of a first embodiment of a dispenser 10 in accordance with the invention that may be used to dispense any type of substance. The dispenser 10 is ideally suited to dispense the substance onto a substrate.

Dispenser 10 generally includes a vial 12 comprising a substantially circular base 14 and a projecting portion 16 extending outward from the base 14. Base 14 has a cavity 18 therein containing the substance 20, while the projecting portion 16 defines a conduit 22 communicating with the cavity 18. More specifically, the conduit 22 aligns with an exit passage 24 of the cavity 18.

Base 14 also includes an annular rim 26 and a holding portion 28 in which the cavity 18 is defined. The projecting portion 16 extends outward from the rim 26. Openings 30 are provided between the holding portion 28 and opposed portions of the rim 26. However, other constructions of the base 14 are envisioned including those in which openings 30 are eliminated.

The holding portion 28 is designed to retain a suitable amount of the substance. When the vial 12 is formed by an injection molding or blow-molding process, it is possible to provide that the cavity 18 can contain up to about 2.5 cc of the substance. When retaining the substance therein, the cavity 18 may be considered as a reservoir.

Figure 2:
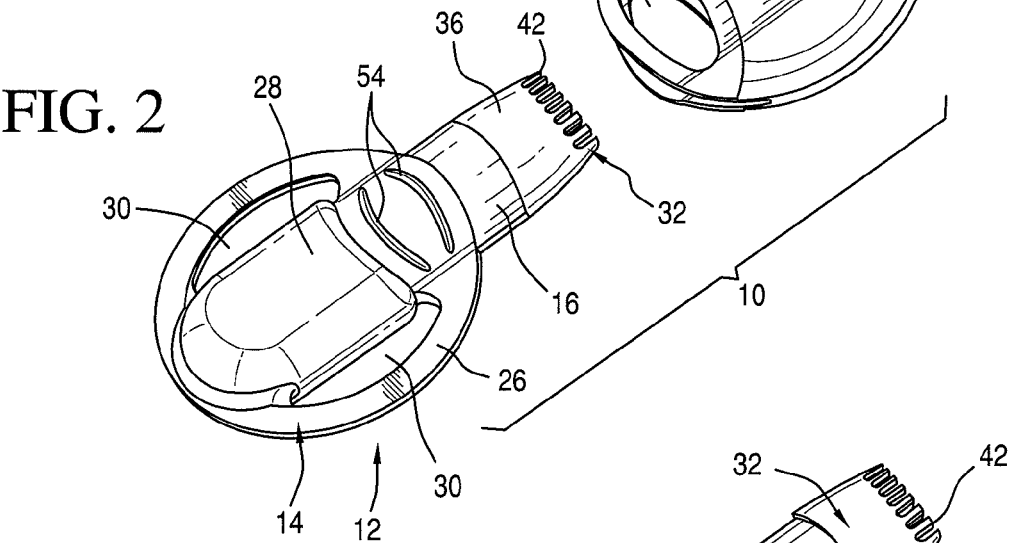
FIG. 2 is an exploded view of the dispenser shown in FIG. 1 showing the cap detached from the base and applicator tip.
Figure 3:
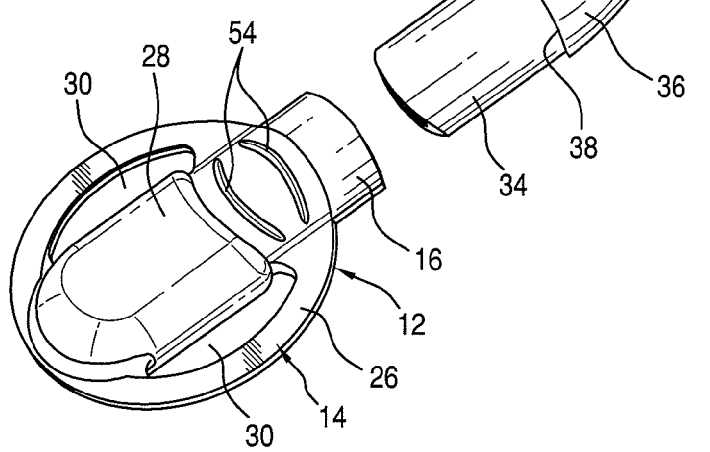
FIG. 3 is a further exploded view of the dispenser shown in FIG. 1 showing the applicator tip detached from the base.
Figure 6:
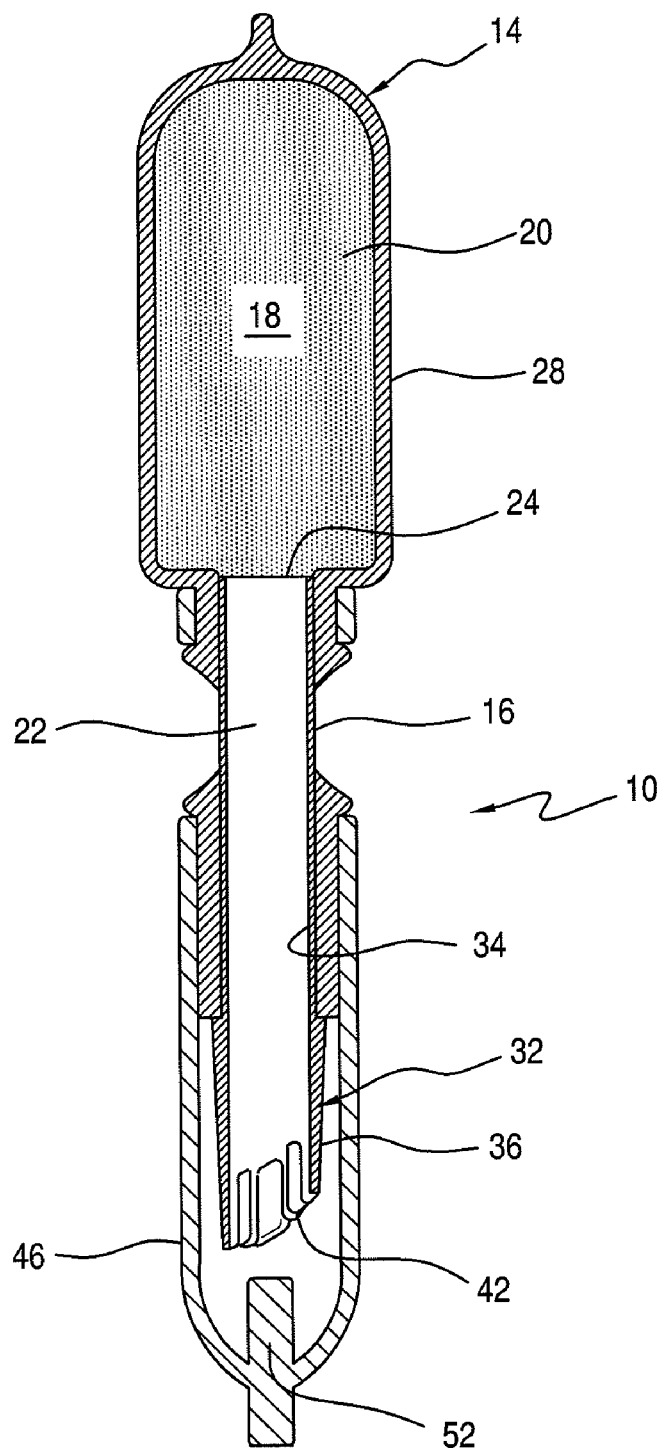
FIG. 6 is a cross-sectional view of the dispenser shown in FIG. 1 taken along the line 6-6 of FIG. 1.

Dispenser 10 also includes an applicator tip 32 having an engagement portion 34 and an applicator portion 36 (see FIG. 3). Engagement portion 34 extends into and through the conduit 22 in the projecting portion 16 and into the exit passage 24 of the cavity 18 (see FIG. 6). A step 38 is defined between the engagement portion 34 and the applicator portion 36 and abuts against a front edge of the projecting portion 16 when the applicator tip 32 is inserted into the conduit 22 to thereby cause the applicator portion 36 to extend forward of the projecting portion 16 (see FIG. 2).

Applicator tip 32 includes one or more internal passages to enable the substance contained in the cavity 18 to flow therethrough to be dispensed. In one embodiment, there are a plurality of internal passages in the engagement portion 34, e.g., three axially extending, parallel passages, and a single internal passage 40 in the applicator portion 36 communicating with all of the internal passages in the engagement portion 34.

Figure 4:
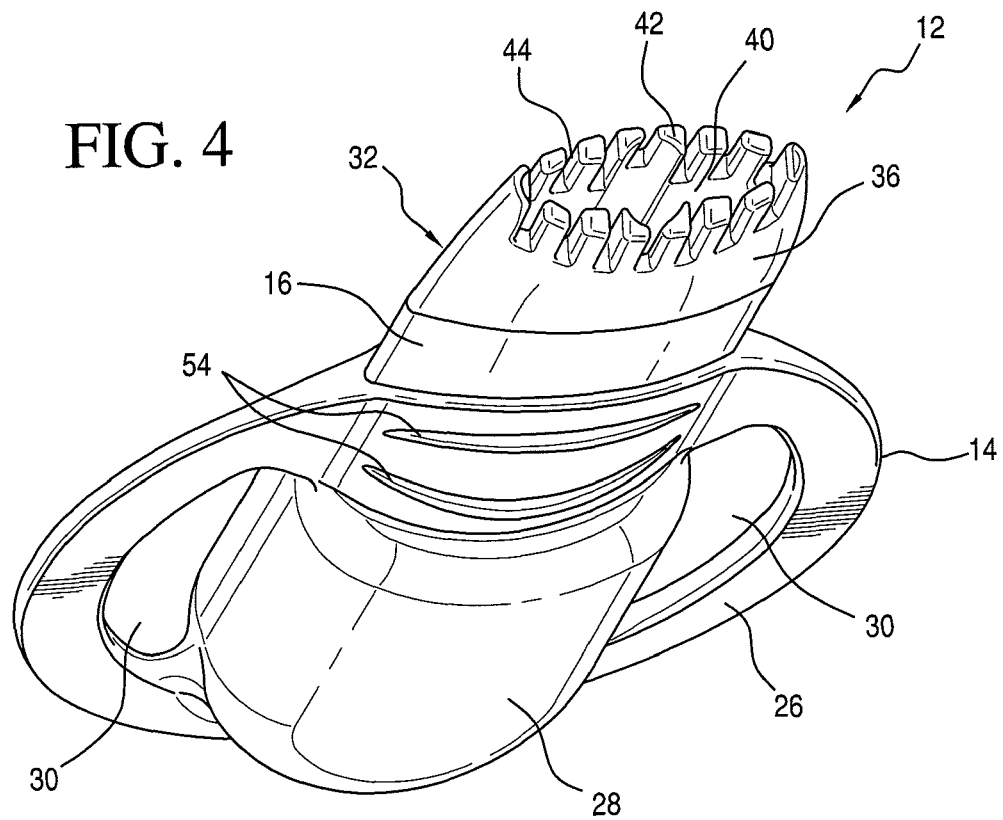
FIG. 4 is a front perspective view of the dispenser shown in FIG. 1 with the cap removed.
Figure 5:
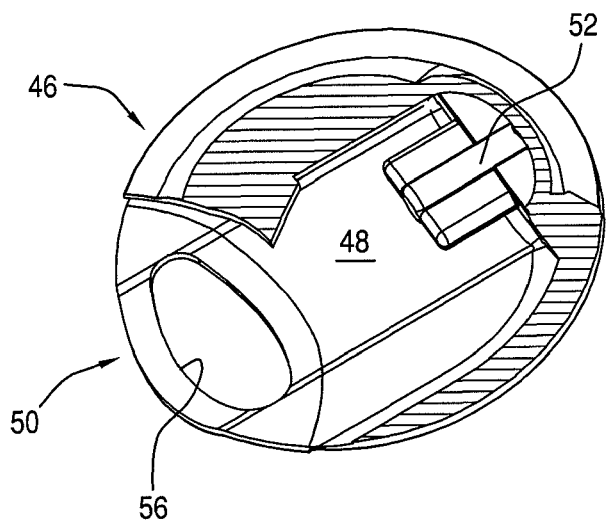
FIG. 5 is a cross-sectional view of the cap of the dispenser shown in FIG. 1.

The internal passage 40 of the applicator portion 36 has a particular cross-sectional shape in a preferred embodiment wherein it includes a long extension in one direction and a short extension in a perpendicular direction and which intersects the long extension at an approximate middle part of each extension (see FIG. 4). This shape aids in an even dispensing of the substance from the cavity 18.

Applicator portion 36 includes a plurality of spaced-apart projections 42 at a distal application surface that define part of the passage 40 therebetween (see FIG. 4). The projections 42 preferably comprise crenellated fingers, i.e., the height of the fingers varies such that a forward edge of each finger is on a virtual plane at an angle other than 90° to a longitudinal axis of the vial 12. The presence of spaces 44 between the fingers improves retention of the substance 20 at the distal application surface of the applicator tip 32. Even further, the combination of the projections 42 formed as crenellated fingers and the spaces 44 therebetween facilitate improved retention of the substance 20, in particular various gels used for application to teeth and/or gums, at the distal application surface of the applicator tip 32 and distribution of the substance 20 over the surface of the teeth or gums.

Dispenser 10 also includes a cap 46 including a cavity 48, an opening 50 on an inner side leading into the cavity 48, and a sealing stopper 52 extending into the cavity 48 toward the opening 50 (see FIGS. 5 and 7-9). Cap 46 is substantially circular such that when attached to the vial 12 and covering the applicator portion 36, the dispenser 10 has the form of the number eight.

Cap 46 is removably attached to the vial 12. When attached, the cap 46 accommodates the applicator portion 36 of the applicator tip 32 in the cavity 48 and the sealing stopper 52 extends into the internal passage of the applicator portion 36. To enable it to seal the internal passage 40 of the applicator portion 36, sealing stopper 52 has a particular cross-sectional that generally corresponds to the cross-sectional shape of the internal passage 40.

In use, the cap 46 is removed from engagement with the vial 12, and the holding portion 28 is held and squeezed causing the substance in the cavity 18 to be urged out through the internal passages of the applicator tip 32 and onto the projections 42 and/or into the spaces 44 therebetween. Then, the dispenser 10 can be manipulated to bring the projections 42 into contact with a substrate to be treated with the substance, e.g., teeth to be treated with a whitening composition.

The dispenser 10 may be made of various materials and processes. As noted above, the base 14 may be made using an injection-molding or blow-molding process from a plastic material capable of being injection-molded or blow-molded, e.g., polypropylene. The applicator tip 32 may be made of an elastomeric material, such as silicone, and provided with appropriate physical properties to enable it to be inserted into the conduit in the base. For example, the cross-sectional shape and size of the engagement portion 34 of the applicator tip 32 may be selected to friction fit into the conduit 22 of the projecting portion 16. Moreover, with the foregoing construction of the vial 12, when a user presses the holding portion 28 thereof, the substance 20 is dispensed but then when the user subsequently releases the pressing force, the substance 20 is not drawn back into the cavity 18.

The particular materials selected for the applicator portion 36 may depend on the substance being dispensed and the substrate onto which it is being dispensed. For example, when the substance is a tooth whitening composition or other material being applied to teeth or gums, the applicator portion 36 is preferably made from a soft elastomeric material to prevent injury to the gums or gums.

The vial 12 and the cap 46 include a cooperating securing mechanism for releasably securing the cap 46 to the vial 12, and more particularly to the base 14.

As shown in FIG. 2, the securing mechanism includes a pair of oppositely curved ridges 54 formed on opposed upper and lower surfaces of the base 14 and apertures 56 formed on the cap 46 to receive the ridges 54 (see also FIGS. 7-9). However, the securing mechanism may include only a single ridge on the base 14 and an abutting surface on a portion of the cap 46 that is positioned to abut against a rear facing surface of the ridge to thereby prevent inadvertent rearward movement of the vial 12 relative to the cap 46 and thus disengagement of the vial 12 and cap 46 from one another, in the absence of manual force urging the ridge under the abutting surface.

Referring now to FIGS. 10-17, a second embodiment of a dispenser in accordance with the invention is designated 58 and differs from the dispenser 10 generally in the construction of the vial. Dispenser 58 includes a vial 60 that has a cavity 62 in which the substance 64 is contained and a squeezable portion 66 that when squeezed, urges the substance 64 out of the cavity 62 into an internal, dispensing channel 68, and an applicator tip 70 onto which the substance is urged and which can be brought into contact with the substrate onto which the substance is being dispensed. The same cap 46 as described above is used in dispenser 58, and removably attaches to the vial 60 and closes the dispensing channel 68.

More particularly, the vial 60 has a substantially circular portion 72 and a conduit 74 extending outward from the circular portion 72, and which defines part of the internal channel 68. Conduit 74 has a substantially oval cross-sectional shape. Circular portion 72 includes a support portion 76 along a partial circumferential edge of the circular portion 72, and an arcuate support rim 78 connected to opposite sides of the support portion 76 and extending over the remaining circumferential edge of the circular portion 72 to thereby complete the circular form of circular portion 72. A remaining part of the internal channel 68 is defined in the support portion 76. Cross supports 80 extend from the support portion to opposite inner edges of the support rim 78 and thereby define open areas 82, 84, 86 between the support portion 76, the support rim 78 and the cross supports 80.

Figure 11:
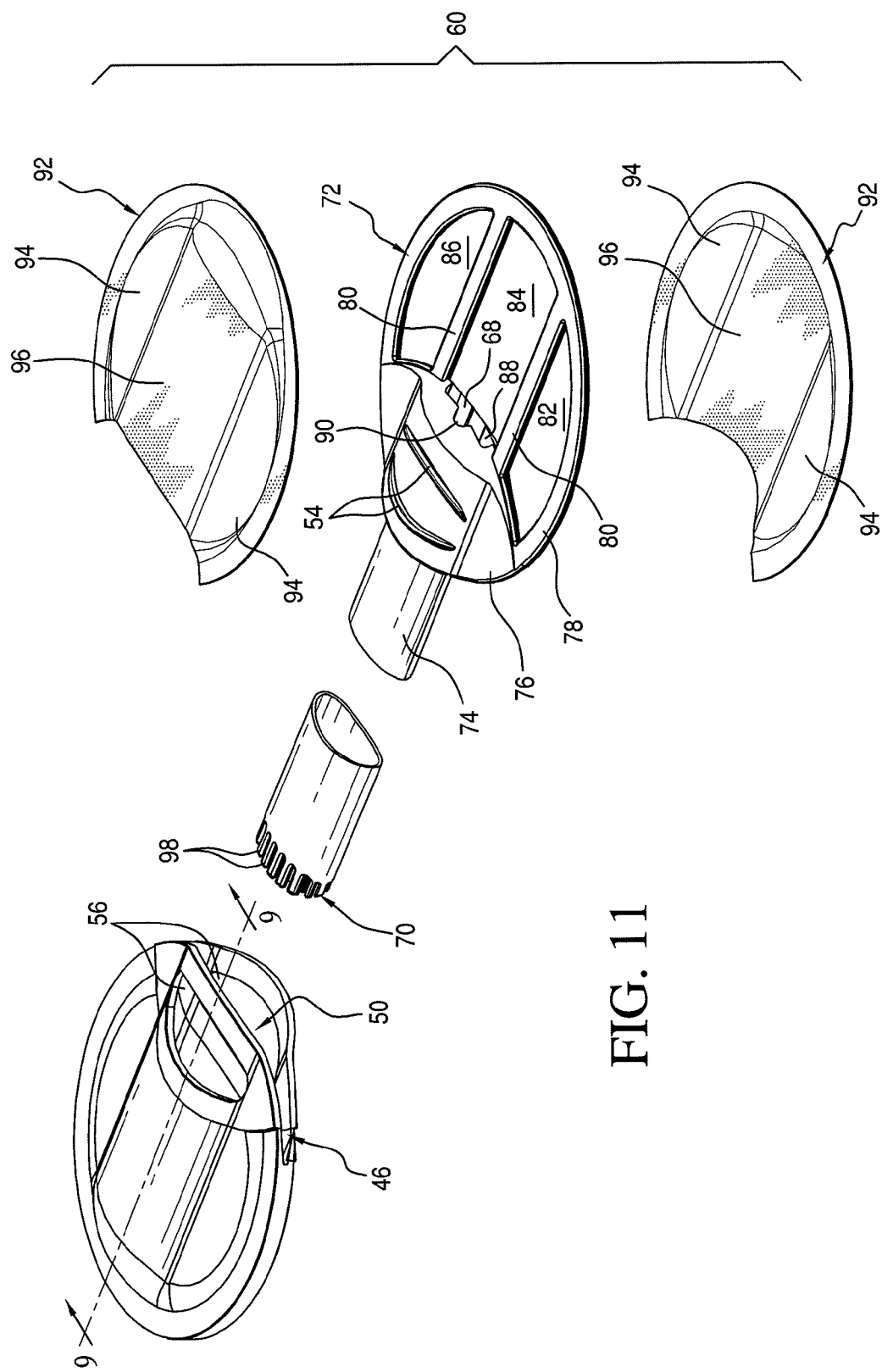
FIG. 11 is an exploded isometric view of the dispenser shown in FIG. 10.

As shown, the internal channel 68 has a particular cross sectional shape with larger horizontal legs 88 than vertical legs 90 (see FIG. 11). However, the cross-sectional shape of the internal channel 68 may vary, subject only to the requirement that it easily enable a flow of the substance in the cavity 62 therethrough upon application of pressure to opposed surfaces of the squeezable portion 66 of the vial 60.

Circular portion 72 of the vial 60 also includes a pair of partially flexible members 92 each arranged on a respective side of the support rim 78 and attached to the support portion 76 and/or support rim 78 to form the cavity 62. Cavity 62 is thus formed between inner surfaces of the members 92 and between the cross supports 80.

Each member 92 has a shape substantially conforming to a shape of the support rim 78, when viewed from above, i.e., generally crescent-shaped. Thus, when attached to the support portion 76 and/or support rim 78, the members 92 can lie substantially flush with the support portion 76 without any gap therebetween. Moreover, each member 92 has first and second flange portions 94 that are substantially planar and an arcuate portion 96 therebetween extending outward from a plane in which the flange portions 94 are arranged (see FIG. 13). When attached to the support portion 76 and/or support rim 78, the first and second flange portions 94 are each arranged between a respective cross support 80 and an adjacent portion of the support rim 78, and the arcuate portion 96 is arranged between the cross supports 80 and extends outward.

The arcuate portions 96 of the members 92 are flexible or otherwise constructed to be squeezable toward one another so that when squeezed, the substance 64 can be urged out of the cavity 62 and into and through the internal channel 68 in communication therewith. Members 92 preferably contact the cross supports 80 to thereby prevent flow of the substance 64 from the cavity 62 around the cross supports 80 into the flange areas of the circular portion 72 of the vial 60 defined between the flange portions 94 of the members 92.

The members 92 provide the circular portion 72 of the vial 60 with opposed substantially circular surfaces that are variably spaced apart from one another, i.e., a smaller spacing in the areas of flange portions 94 than arcuate portions 96, and form the cavity 62 between opposed portions of the circular surfaces. Moreover, the circular surfaces have an undulating form with low points at lateral edges of the circular portion 72 (i.e., at the edges of the flange portions 94) and a high point in a center of the circular portion (i.e., at the center of the arcuate portion 96), as shown in FIG. 13. The circular surfaces gently slope between the low points and the high point.

The applicator tip 70 is elongate and arranged over the conduit 74, and to provide a tight fit over conduit 74, the applicator tip 70 may have substantially the same cross-sectional shape as the conduit 74, i.e., oval as shown. A distal end of the applicator tip 70 includes projections 98 that are adapted to contact the substrate. The applicator tip 70 may be overmolded onto the conduit 74 such that a portion of the applicator tip 70 including the projections 98 extends beyond an axial edge of the conduit 74.

Projections 98 may be in the form of crenellated fingers arranged to provide a bush-like, even spreading of the substance 62 onto the substrate, see FIG. 17. The crenellated fingers may be arranged to form two or more oval or annular rows, each pair of adjacent rows being separated by a channel 100. The projections 98 and channel 100 cooperate to define retention areas in which the substance 62 is retained ready for application to the substrate.

In a preferred embodiment shown in FIG. 15, the projections 98 have a variable axial length from a largest axial length on one side of the applicator tip 70 to a shortest axial length on an opposite side of the applicator tip 70.

Various materials may be used to form the components described above. For example, the circular portion 72 of the vial 60 may be made of high density polyethylene (HDPE), the members 94 may be made of film or foil, the applicator tip may be made of a soft material such as silicone.

Possible substances for dispensing via dispensers 10, 58 onto a substrate include, but are not limited to, dispensing of toothpaste or dentifrice onto teeth, dispensing of whitening gel onto teeth, dispensing of a tooth desensitizing material onto teeth, dispensing of a topical compound to skin, dispensing of a pharmaceutical skin product to skin, and dispensing of adhesive onto a surface to be adhered to something else.

While the foregoing description and drawings represent the preferred embodiments of the present invention, it will be understood that various changes and modifications may be made without departing from the scope of the present invention.

The invention claimed is:

1. A dispenser for dispensing a substance, comprising:
a vial comprising a substantially circular base having a cavity therein containing the substance and a projecting portion extending outward from said base and defining a conduit communicating with said cavity;
an applicator tip arranged partly alongside said conduit and including at least one internal passage communicating with said cavity, said applicator tip including an applicator portion situated forward of said conduit, said applicator portion including a plurality of spaced-apart projections at a distal application surface; and
a cap including an opening, a cavity communicating with said opening and a sealing stopper extending into said cavity toward said opening, said cap being removably attachable to said vial and when attached to said vial, said cavity of said cap accommodating said applicator portion of said applicator tip and said sealing stopper extending into said at least one internal passage so that said cap seals said at least one internal passage of said applicator tip,
whereby when said cap is removed from said vial and said base is squeezed, the substance in said cavity is urged out of said cavity through said at least one internal passage of said applicator tip and onto said projections.

2. The dispenser of claim 1, wherein said applicator tip is arranged partly in said conduit.

3. The dispenser of claim 1, wherein said base includes an annular rim and a main portion defining said cavity and spaced apart from opposed portions of said rim, said projecting portion extending outward from said rim.

4. The dispenser of claim 1, wherein said projections comprise crenellated fingers.

5. The dispenser of claim 1, wherein said applicator tip is made of silicone and said vial is made of polypropylene.

6. The dispenser of claim 1, wherein said at least one internal passage in said applicator tip comprises a first passage extending distally from a proximal end of said applicator tip and a second passage at a distal end of said applicator tip, said second passage having a cross-section defined by a long leg and a short leg intersecting at an approximate middle part, said cap including a sealing stopper having substantially the same cross-sectional shape as said second passage and being arranged to enter into said second passage when said cap is attached to said vial.

7. The dispenser of claim 1, wherein said cap is substantially circular and configured to be attached to said base such that said dispenser has the form of the number eight.

8. The dispenser of claim 1, wherein said cap includes a securing mechanism for releasably securing said cap to said vial.

9. The dispenser of claim 1, wherein said projecting portion of said vial is arranged to enter into said cavity of said cap through said opening of said cap when said cap is attached to said vial, whereby at least part of said projecting portion is accommodated in said cavity of said cap.

10. A dispenser for dispensing a substance, comprising:
a vial defining a cavity in which the substance is arranged, said vial including a base and a projecting portion extending outward from said base, said projecting portion including a conduit communicating with said cavity;
an applicator tip arranged partly in said conduit and including at least one internal passage communicating with said cavity, said applicator tip including an applicator portion made of an elastomeric material and situated exterior of said conduit, said applicator portion including a plurality of spaced-apart projections at a distal application surface; and
a cap including an opening and a cavity communicating with said opening, said cap being removably attachable to said vial and when attached to said vial, said cavity of said cap accommodating said applicator portion of said applicator tip so that said cap seals said at least one internal passage of said applicator tip,
whereby when said cap is removed from said vial and said base is squeezed, the substance in said cavity is urged out of said cavity through said at least one internal passage of said applicator tip and onto said projections.

11. The dispenser of claim 10, wherein said base is substantially circular and includes an annular rim and a main portion defining said cavity and spaced apart from opposed portion of said rim, said projecting portion extending outward from said rim.

12. The dispenser of claim 10, wherein said applicator tip further includes an engagement portion arranged within said conduit of said projection portion, said engagement portion having an outer surface that contacts an inner surface defining said conduit.

13. The dispenser of claim 10, wherein said projections comprise crenellated fingers.

14. The dispenser of claim 10, wherein said at least one internal passage in said applicator tip comprises a first passage extending distally from a proximal end of said applicator tip and a second passage at a distal end of said applicator tip, said second passage having a cross-section defined by a long leg and a short leg intersecting at an approximate middle part, said cap including a sealing stopper having substantially the same cross-sectional shape as said second passage and being arranged to enter into said second passage when said cap is attached to said vial.

15. The dispenser of claim 10, wherein said base and said cap are substantially circular and said cap is configured to be attached to said base such that said dispenser has the form of the number eight.

16. The dispenser of claim 10, wherein said cap includes a securing mechanism for releasably securing said cap to said vial.

17. The dispenser of claim 10, wherein said projecting portion of said vial is arranged to enter into said cavity of said cap through said opening of said cap when said cap is attached to said vial, whereby at least part of said projecting portion is accommodated in said cavity of said cap.

* * * * *